(12) United States Patent
Oraevsky et al.

(10) Patent No.: US 6,405,069 B1
(45) Date of Patent: Jun. 11, 2002

(54) TIME-RESOLVED OPTOACOUSTIC METHOD AND SYSTEM FOR NONINVASIVE MONITORING OF GLUCOSE

(75) Inventors: Alexander A. Oraevsky, Houston; Alexander A. Karabutov, Galveston, both of TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 09/412,852

(22) Filed: Oct. 6, 1999

Related U.S. Application Data

(63) Continuation-in-part of application No. 09/179,791, filed on Oct. 27, 1998, now Pat. No. 6,309,352, which is a continuation-in-part of application No. 08/594,758, filed on Jan. 31, 1996, now Pat. No. 5,840,023.

(51) Int. Cl.[7] .............................. A61B 6/00; G03B 42/06
(52) U.S. Cl. .............................. 600/407; 600/316; 367/7
(58) Field of Search .................................. 600/407, 437, 600/316, 310, 586, 322, 438, 478, 319; 606/3, 10, 11, 13; 73/587, 606; 367/7

(56) References Cited

U.S. PATENT DOCUMENTS

| | | |
|---|---|---|
| 4,028,933 A | 6/1977 | Lemons et al. |
| 4,212,206 A | 7/1980 | Hartemann et al. |
| 4,255,971 A | 3/1981 | Rosenewaig |
| 4,267,732 A | 5/1981 | Quate |
| 4,385,634 A | 5/1983 | Bowen et al. |
| 4,430,897 A | 2/1984 | Quate |
| 4,594,662 A | 6/1986 | Devaney |
| 4,710,030 A | 12/1987 | Tauc et al. |
| 4,727,420 A | 2/1988 | Kohda et al. |
| 5,041,121 A | 8/1991 | Wondrazek et al. |
| 5,070,874 A | 12/1991 | Barnes et al. |
| 5,136,172 A | 8/1992 | Nakata et al. |
| 5,141,331 A | 8/1992 | Oehler et al. |
| 5,158,560 A | 10/1992 | Sogawa et al. |
| 5,161,125 A | 11/1992 | Maccabee |
| 5,178,836 A | 1/1993 | Kitamori et al. |
| 5,207,672 A | 5/1993 | Roth et al. |
| 5,222,496 A | 6/1993 | Clarke et al. |
| 5,254,112 A | 10/1993 | Sinofsky et al. |
| 5,293,873 A | * 3/1994 | Fang ........................... 600/437 |
| 5,348,002 A | * 9/1994 | Caro ........................... 600/310 |
| 5,398,685 A | 3/1995 | Wilk et al. |
| 5,421,337 A | 6/1995 | Richards-Kortum et al. |
| 5,444,541 A | 8/1995 | Small et al. |
| 5,465,722 A | * 11/1995 | Fort et al. .................... 600/447 |
| 5,481,113 A | 1/1996 | Dou et al. |
| 5,492,118 A | 2/1996 | Gratton et al. |
| 5,551,422 A | 9/1996 | Simonsen et al. |
| 5,554,810 A | 9/1996 | Anifrani et al. |
| 5,560,356 A | * 10/1996 | Peyman ....................... 600/316 |

(List continued on next page.)

FOREIGN PATENT DOCUMENTS

| | | |
|---|---|---|
| WO | WO 97/27801 | 8/1997 |
| WO | WO 98/38904 | 9/1998 |

OTHER PUBLICATIONS

Esenaliev et al., "Axial Resolution of Laser Optoacoustic Imaging: Influence of Acoustic Attenuation and Diffraction," *SPIE*, 3254:294–306 (1998).

(List continued on next page.)

*Primary Examiner*—Marvin M. Lateef
*Assistant Examiner*—Shawna J Shaw
(74) *Attorney, Agent, or Firm*—Braman & Rogalskyj, LLP

(57) ABSTRACT

The present invention is directed to a method/system of monitoring in real time changes in concentration of glucose in tissues. Laser-induced profiles of absorbed optical energy distribution in tissues are determined via measurements of spatial (in-depth) profile of optically-induced acoustic (pressure) transients using a wide-band optoacoustic transducer. Such technique can be applied for monitoring of glucose concentration in various human or nonhuman tissues, cell cultures, solutions or emulsions.

19 Claims, 7 Drawing Sheets

U.S. PATENT DOCUMENTS

| | | | |
|---|---|---|---|
| 5,582,578 A | 12/1996 | Zhong et al. | |
| 5,583,634 A | 12/1996 | Andre et al. | |
| 5,588,428 A | 12/1996 | Smith et al. | |
| 5,602,894 A | 2/1997 | Bardash | |
| 5,615,672 A | 4/1997 | Braig et al. | |
| 5,615,675 A * | 4/1997 | O'Donnell et al. | 600/425 |
| 5,657,754 A | 8/1997 | Rosencwaig | |
| 5,662,590 A | 9/1997 | de la Torre et al. | |
| 5,692,504 A | 12/1997 | Essenpreis et al. | |
| 5,713,356 A | 2/1998 | Kruger | |
| 5,718,231 A | 2/1998 | Dewhurst et al. | |
| 5,722,406 A | 3/1998 | Papaioannou | |
| 5,770,454 A | 6/1998 | Essenpreis et al. | |
| 5,782,755 A | 7/1998 | Chance et al. | |
| 5,796,476 A | 8/1998 | Wang et al. | |
| 5,830,139 A * | 11/1998 | Abreu | 600/400 |
| 5,835,215 A | 11/1998 | Toida et al. | |
| 5,840,023 A * | 11/1998 | Oraevsky et al. | 600/407 |
| 5,871,442 A | 2/1999 | Madarasz et al. | |
| 5,882,301 A | 3/1999 | Yoshida | |
| 5,896,198 A | 4/1999 | Chou et al. | |
| 5,897,494 A | 4/1999 | Flock et al. | |
| 5,902,237 A | 5/1999 | Glass | |
| 5,924,986 A | 7/1999 | Chandler et al. | |
| 5,938,617 A * | 8/1999 | Vo-Dinh | 600/476 |
| 5,941,821 A | 8/1999 | Chou | |
| 5,944,687 A | 8/1999 | Benett et al. | |
| 5,977,538 A | 11/1999 | Unger et al. | |
| 6,022,309 A * | 2/2000 | Celliers et al. | 600/7 |
| 6,070,093 A * | 5/2000 | Oosta et al. | 600/316 |
| 6,278,889 B1 * | 8/2001 | Robinson | 600/322 |
| 6,285,894 B1 * | 9/2001 | Oppelt et al. | 600/322 |
| 6,309,352 B1 * | 10/2001 | Oraevsky et al. | 600/407 |

OTHER PUBLICATIONS

Oraevsky, et al., "Laser Optacoustic Tomography of Layered Tissues: Signal Processing", *SPIE*, 2979:59–70 (1997).

Esenaliev et al., "Laser Optoacoustic Imaging for Breast Cancer Diagnostics: Limit of Detection and Comparison with X–ray and Ultrasound Imaging," *SPIE*, 2979:71–82 (1997).

Oraevsky et al., "Measurement of Tissue Optical Properties by Time–Resolved Detection of Laser–Induced Transient Stress," *Applied Optics*, 36(1):402–415 (1997).

Agah et al., "Dynamics of Temperature Dependent Optical Properties of Tissue: Dependence on Thermally Induced Alteration," *IEEE Transactions on Biomedical Engineering*, 43(8):839–846 (1996).

Esenaliev et al., "Laser Opto–acoustic Tomography for Medical Diagnostics: Experiments with Biological Tissues," *SPIE*, 2676:84–90 (1996).

Karabutov et al., "Time–resolved Laser Optoacoustic Tomography of Inhomogeneous Media," *Appl. Phys. B*, 63:545–563 (1996).

Kim et al., "Nonlinear Finite–Element Analysis of the Role of Dynamic Changes in Blood Perfusion and Optical Properties in Laser Coagulation of Tissue," *IEEE Journal of Selected Topics in Quantum Electronics*, 2(4):922–933 (1996).

Oraevsky et al., "Laser Opto–Acoustic Imaging of Turbid Media: Determination of Optical Properties by Comparison With Diffusion Theory and Monte Carlo Simulation," *SPIE*, 2681:277–284 (1996).

Oraevsky et al., "Laser Opto–Acoustic Tomography for Medical Diagnostics: Principles," *SPIE*, 2676:22–31 (1996).

Oraevsky et al., "Breast Cancer Diagnostics by Laser Opto–Acoustic Tomography," in Alfano et al., ed., *Trends in Optics and Photonics. TOPS vol. II. Advances in Optical Imaging and Photon Migration*, pp. 316–321 (1996).

Oraevsky, "Laser Optoacoustic Imaging for Diagnostics of Cancer," *LEOS Newsletter*, pp. 17–20 (Dec. 1996).

Motamedi et al. "Laser Photocoagulation of Prostate: Influence of Dosimetry," *Lasers in Surgery and Medicine*, 17:49–58 (1995).

Oravesky et al., "Lateral and Z–Axial Resolution in Laser Optoacoustic Imaging With Ultrasonic Transducers," *SPIE*, 2389:198–208 (1995).

Vijverberg et al., Evaluation of a Time–resolved Stress Detection Method to Determine Tissue Optical Properties, *Proc. SPIE*, 2323:312–316 (1995).

Oraevsky et al., "Time–Resolved Optoacoustic Imaging in Layered Biological Tissues," in Alfano, ed., *OSA Proceedings on Advances in Optical and Photon Migration*, 21:161–165 (1994).

Oravesky et al., "Laser–Based Optoacoustic Imaging in Biological Tissues," *SPIE*, 2134:122–128 (1994).

Thomsen et al., "Optical Properties of Albino Rat Skin Heated In Vitro: Comparison of Photoacoustic and Integrating Sphere Measurement Techniques," *SPIE*, 2134A:106–113 (1994).

Oraevsky et al., "Determination of Tissue Optical Properties by Piezoelectric Detection of Laser–Induced Stress Waves", *SPIE*, 1882:86–101 (1993).

Kohl et al., "Influence of Glucose Concentration on Light Scattering In Tissue–Simulating Phantoms", *Optics Letters*, 19(24)2170–2172 (1994).

Maier et al., "Possible Correlation Between Blood Glucose Concentration and the Reduced Scattering Coefficient of Tissues in the Near Infrared", *Optics Letters*, 19(24):2062–2064 (1994).

Oraevsky et al., "Laser–Based Optoacoustic Imaging in Biological Tissues," *SPIE*, 2134A:122–128 (1994).

Kohl et al., "The Influence of Glucose Concentration Upon the Transport of Light in Tissue–Simulating Phantoms," *Phys. Med. Biol.*, 40:1267–1287 (1995).

Tuchin et al., "Light Propagation in Tissues with Controlled Optical Properties," *SPIE*, 2925:118–142 (1996).

Coté, "Noninvasive Optical Glucose Sensing—An Overview," *Journal of Clinical Engineering*, 22(4):253–259 (1997).

Bednov et al., "Opto–Acoustic System for Glucose Monitoring in Biological Tissues,"p. 41 of abstract book, 17th Annual Houston Conference on Biomedical Engineering Research, sponsored by the Houston Society for Engineering in Medicine and Biology, held Feb. 11–12, 1999, Houston, Texas.

Larin et al., "Optoacoustic Signal Profiles for Monitoring Glucose Concentration in Turbid Media," *SPIE*, 3726:576–583 (1999).

Oravesky et al., "Opto–Acoustic Monitoring of Blood Glucose," p. 17 of abstract book, Advances in Optics for Biotechnology, Medicine and Surgery, sponsored by United Engineering Foundation, Inc., held Aug. 1–6, 1999, Kailua-Kona, Hawaii.

* cited by examiner

TIME-RESOLVED OPTOACOUSTIC METHOD AND SYSTEM FOR NONINVASIVE MONITORING OF GLUCOSE

CROSS-REFERENCE TO RELATED APPLICATION

This patent application is a continuation-in-part of U.S. application Ser. No. 09/179,791, filed Oct. 27, 1989 now U.S. Pat. No. 6,309,352, which is a continuation-in-part of U.S. application Ser. No. 08/594,758, filed Jan. 31, 1996, now U.S. Pat. No. 5,840,023.

BACKGROUND OF THE INVENTION

1. Field of the Invention

The present invention relates generally to the fields of analytical sensing, imaging, and monitoring. More specifically, the present invention relates to a method and system utilizing time-resolved optoacoustic technique to monitor in real time tissue optical properties, which in turn depend on glucose concentration in blood.

2. Description of the Related Art

There is a continued significant effort by many companies and scientific groups to quantify blood glucose concentration with noninvasive and minimally invasive procedures. A number of patents have been issued to protect various noninvasive technologies for glucose monitoring. Noninvasive procedures employ various optical approaches.

In previously disclosed approaches, glucose was detected directly as a chromophore (absorbing molecule), Raman scattering molecule, dichroic (polarization rotating) molecule or fluorescent complex with a strongly fluorescent dye and an osmolyte that changes tissue scattering. All these approaches utilize measurement of signal amplitude in response to tissue irradiation with light. The main weakness of all these pure optical approaches is low signal to noise ratio and/or low specificity to glucose. Low signal to noise ratio results from the fact that glucose is present in tissues in millimolar concentration, while other interfering molecules are present in greater concentrations. Low specificity results from the fact that optical properties of glucose overlap with optical properties of interfering molecules. All previously disclosed methods have one additional inherent limitation associated with incapability to measure changes in optical properties along the photon path inside the tissue. Only signals integrated over the entire optical path in tissue can be determined by standard optical. methods. Time resolved, phase-resolved and interferometric optical methods possess limitations that are not currently resolved.

MacKenzie et al. (WO 98/38904), Rozensweig et al. (U.S. Pat. No. 5,657,754), and Chou (U.S. Pat. No. 5,941,821) disclosed the use of photoacoustic and thermoacoustic spectroscopy for glucose monitoring. These photoacoustic techniques utilize high sensitivity of acoustic detection. However, these technologies determine the concentration of glucose from an acoustic signal amplitude. The method of photoacoustic spectroscopy does not measure neither tissue scattering, nor profiles of optically induced acoustic waves in tissues irradiated under conditions of stress confinement in the tissue volume of interest. The detection of profiles of optically induced acoustic waves instead of detection of either optical amplitude or acoustic amplitude makes a significant difference in the signal-to-noise ratio.

An important ability of glucose to decrease tissue scattering based on its properties as osmolyte was first described by Gratton et al. (U.S. Pat. No. 5,492,118). However, this prior art disclosed pure optical less precise means to measure tissue scattering. These means do not utilize measurement of profiles of spatial distribution of tissue scattering replicated in profiles of acoustic waves, and therefore, can not yield sufficiently sensitive and reliable method to measure glucose concentration in tissues.

The prior art is deficient in the lack of effective means of noninvasive monitoring of glucose concentration in real time. The present invention fulfills this long-standing need and desire in the art.

SUMMARY OF THE INVENTION

The present invention is directed to a method and system of real-time optoacoustic monitoring of tissue optical scattering for the purpose of providing quantitative information about glucose concentration in blood.

In one embodiment of the present invention, there is provided a method of noninvasive monitoring of glucose concentration in real time using laser optoacoustic imaging, comprising the steps of irradiating a tissue of interest with at least one short optical pulse to create a distribution of absorbed optical energy in the tissue; generating optothermally-induced pressure profile under conditions of temporal pressure confinement in the irradiated tissue; detecting the pressure profile with at least one acoustic transducer, wherein the acoustic transducer is a wide-band transducer capable of detecting the entire range of ultrasonic frequencies contained in the pressure profile; recording the ultrasound signal magnitude along the pressure profile by an electronic system; analyzing the spectrum of ultrasonic frequencies of the pressure profile, wherein a change in the ultrasonic frequency indicates a change in tissue scattering coefficient, which in turn is proportional to a change in glucose concentration in the tissue, which further correlates with a change of glucose concentration in blood.

The method disclosed herein can be utilized in systems measuring tissue optical properties in vivo and, in principle, can be applied for detection of other tissue analytes influencing tissue optical properties. In another embodiment of the present invention, there is provided a system for monitoring glucose concentration noninvasively in real time, comprising a pulsed optical source to produce a pressure profile confined in a volume of tissue of interest; a light delivery system for delivery of radiation to the tissue; at least one acoustic transducer to detect the pressure profile in the tissue, wherein the acoustic transducer is capable of detecting the entire range of ultrasonic frequencies contained in the pressure profile; an electronic system for recording and processing of the detected pressure profile; and a computer with software analysis of the detected pressure profile and calculation the glucose concentration.

Other and further aspects, features, and advantages of the present invention will be apparent from the following description of the presently preferred embodiments of the invention given for the purpose of disclosure.

DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

DETAILED DESCRIPTION OF THE INVENTION

Figure 1:
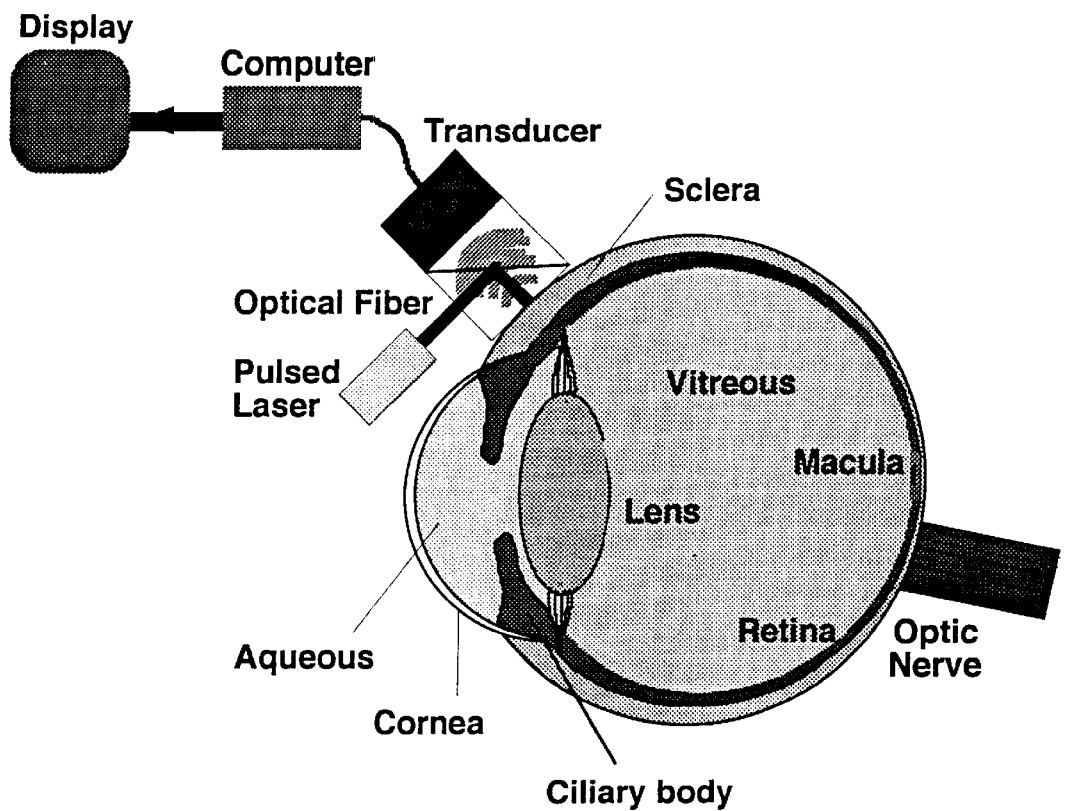
FIG. 1 shows the schematics of the ocular opto-acoustic biosensor.

The present invention is directed to a method and a system of monitoring changes of glucose concentration in tissues in real time. Laser-induced profiles of absorbed optical energy distribution in tissue are determined via measurements of spatial (in-depth) profile of optically-induced acoustic (pressure) transients. The method utilizes variation in tissue optical scattering due to the variation in concentration of glucose and its molecular derivatives and also utilizes irradiation conditions of temporal stress confinement in the irradiated volume in order to achieve exact coincidence between the distribution of absorbed energy and the detected acoustic profile. The wavelength of optical pulses is chosen to achieve maximum value of tissue scattering with simultaneous minimal absorption in order to maximize the measured effect of glucose on tissue scattering. Wide-band acoustic transducers are capable of detecting ultrasonic frequencies in the range from 20 kHz to several hundred MHz and used to allow precise measurement of optoacoustic pressure profiles.

The method for analyzing optoacoustic profiles and their ultrasonic spectra is also disclosed as a means to deduce concentration of tissue glucose with maximum precision. A simple analysis of the recorded optoacoustic profiles consists of fitting its exponential trailing edge with $\exp(-\omega_{ac}t)$, where $\omega_{ac} = \mu_{eff} c_0$ is the effective acoustic frequency, i.e., the ultrasonic frequency corresponding to the detected optoacoustic profile, $c_0$ is the speed of sound in tissue, $\mu_{eff}$ is the effective optical attenuation coefficient defined by tissue optical absorption and tissue optical scattering. In diffusion approximation, the effective attenuation is proportional to the square root of the effective scattering).

A more sophisticated analysis employs a fit of the entire experimentally measured profile with the theoretically calculated profile:

$$P^{tr}(z, \tau, r_\perp = 0) = \frac{\rho^{tr} c_l^{tr}}{\rho_0} \int_0^\infty \frac{\beta^* I_0 N_{ac}(\mu_a c_0)}{C_p(1+N_{ac})} \frac{\omega_{ac}\exp(-\omega_{ac}t) - \omega_D \exp(-\omega_D t)}{\omega_{ac} - \omega_D} L(\tau - t) dt$$

where $\omega_D = 2(z^{tr} c_l^{tr})/a_0^2$ is the characteristic ultrasonic frequency of acoustic diffraction, defined by the radius of acoustic wave (equal to the radius of laser beam), speed of sound in the optoacoustic prism, $c_l^{tr}$ and distance propagated by acoustic wave in the optoacoustic prism, $Z^{tr}$. Acoustic diffraction in a tissue is negligible compared with the acoustic diffraction in the optoacoustic prism. Function L(t) describes the temporal response of the acoustic transducer to the laser pulse employed to irradiate tissue. In order to extract quantitative information about $\omega_{ac}$ in the laser-irradiated tissue, one needs to deconvolute the measured optoacoustic profile and the temporal response of the acoustic transducer, L(t).

In one embodiment of the present invention, there is provided a method of noninvasive monitoring of glucose concentration in real time using laser optoacoustic imaging, comprising the steps of irradiating a tissue of interest with at least one short optical pulse to create a distribution of absorbed optical energy in the tissue; generating optothermally-induced pressure profile under conditions of temporal pressure confinement in the irradiated tissue; detecting the pressure profile with at least one acoustic transducer, wherein the acoustic transducer is capable of detecting the entire range of ultrasonic frequencies contained in the pressure profile; recording an amplitude and temporal profile of the pressure profile by an electronic system; analyzing ultrasonic frequency of the pressure profile, wherein a change in the ultrasonic frequency indicates a change in tissue scattering coefficient, which in turn is proportional to a change in glucose concentration in the tissue, which further correlates with a change of glucose concentration in blood.

Preferably, the tissue is selected from the group consisting of sclera, ear lobe, finger, etc. For the purposes of this method and system, the term "tissue" may also comprise a turbid medium such as a cell culture, an emulsion or other optically turbid medium. More preferably, the optical pulse is generated from a laser or non-laser source and is in the spectral range from about 0.2 µm to about 20 µm. A plurality of pulsed optical sources and/or a multitude of irradiation wavelengths can be used to perform differential measurements and enhance the accuracy of determined glucose concentration. A representative acoustic transducer is a wide-band acoustic transducer, operating in the frequency range from 900 KHz to 200 MHz. If it is desirable to determine a geometry of the monitored tissue in addition to the determination of glucose concentration, a multiple of acoustic transducers may be positioned at fixed locations along the surface of the monitored tissue.

The in depth pressure profile in the irradiated tissue can be detected by measuring temporal profile of the optoacoustic signal with a single transducer. The pressure profile detection occurs at a tissue depth of up to about 12 cm measured from an irradiated surface and is performed either in forward signal propagation mode as the irradiation and the acoustic detection are performed a t different sites in the tissue or in backward signal propagation mode as the irradiation and the acoustic detection are performed at a same site.

Scanning of the acoustic transducer along the tissue or by scanning of an array of transducers along the same tissue can help to determine glucose, concentration at various locations and various tissues. The pressure profile is recorded simultaneously from a number of sites along a surface of the tissue in order to reconstruct a two-dimensional or three-dimensional topographic image of glucose distribution in tissue. Furthermore, multiple separate optical fibers or laser beams irradiate a large volume of tissue to reduce time of scanning and incident laser fluence, wherein the preferred irradiating is in a spectral range of from about 300 nm to about 2400 nm.

The noninvasive monitoring method further comprises the step of administering an exogenous substance to the tissue so that the exogenous substance reacts selectively with glucose and enhances the effect of glucose on tissue scattering. Representative examples of such exogenous substance can be chosen from the class of substances strongly changing optical refractive index of tissue and selectively binding to glucose.

In another embodiment of the present invention, there is provided a system for monitoring glucose concentration noninvasively in real time, comprising a pulsed optical source to produce a pressure profile confined in a volume of tissue of interest; a light delivery system for delivery of radiation to the tissue; at least one acoustic transducer to detect the pressure profile in the tissue, wherein the acoustic transducer is capable of detecting the entire range of ultrasonic frequencies contained in the pressure profile; an electronic system for recording and processing of the detected pressure profile; and a computer with software for analysis of the detected pressure profile and (if needed) for image reconstruction. Preferably, the pulsed optical source generates optical pulses as short as measured in nanoseconds. Still preferably, the acoustic transducer is a wide-band acoustic transducer.

The following examples are given for the purpose of illustrating various embodiments of the invention and are not meant to limit the present invention in any fashion.

EXAMPLE 1
Ocular Opto-Acoustic Biosensor

A modification of the disclosed system is used for monitoring of glucose in human sclera (FIG. 1). The major component of the sensor is the opto-acoustic front surface transducer. A Q-switched Nd:YAG laser here is a source of ultraviolet pulses at the wavelength of 355-nm. A quartz optical fiber is employed to transmit laser pulses through the opto-acoustic prism and to the surface of the sclera. An opto-acoustic prism (made optically and acoustically transparent, usually of quartz) allows an incorporation of the optical and the acoustic components of the sensor in one system, in order to detect acoustic waves at the site of optical irradiation. An optical collimator may be employed to concentrate the optical energy onto the tissue in contact with the opto-acoustic prism. The optical pulsed energy propagates in the tissue of sclera and generates acoustic (pressure) transient. Wide-band ultrasound waves generated by optical pulses in tissue propagate to the acoustic detector.

It is demonstrated that if laser pulses are sufficiently short, the generated optoacoustic profile accurately replicates the initial profile of absorbed optical energy. Optoacoustic profile represents the shape of acoustic (pressure) temporal waveform generated in response to pulsed irradiation under conditions of stress confinement in the irradiated tissue volume of interest. The optoacoustic profile depends on optical scattering coefficient in tissue. Variation in optical scattering in certain human tissues is defined by the variation in glucose concentration, which in turn directly proportional to the glucose concentration in the blood. The laser-induced acoustic wave propagates from sclera through the opto-acoustic prism to a wide-band piezoelectric transducer, capable of detection the entire range of ultrasonic frequencies in the laser-induced acoustic wave. Only acoustic waves generated at the site of laser irradiation can propagate within the angle of acceptance of the piezoelectric transducer. The sensor utilizes a piezoelectric crystal as a detector operating within a wide-band of ultrasound frequencies. However, a fiberoptic interferometer can also be used.

The detected signal is then transmitted to an electronic data acquisition and analysis system, capable of analyzing both the temporal profiles of detected signals and their ultrasonic spectra.

The analysis of the recorded optoacoustic profiles is aimed at determining $\omega_{ac}$ with maximum precision. The procedure consists of either fitting its exponential trailing edge with $\exp(-\omega_{ac}t)$, where $\omega_{ac}=\mu_{eff}c_0$ is the effective acoustic frequency, or fitting of the entire experimentally measured profile with the theoretically calculated profile:

$$P^{tr}(z, \tau, r_\perp = 0) = \frac{\rho^{tr}c_l^{tr}}{\rho_0} \int_0^\infty \frac{\beta^* I_0 N_{ac}(\mu_a c_0)}{C_p(1+N_{ac})} \frac{\omega_{ac}\exp(-\omega_{ac}t) - \omega_D\exp(-\omega_D t)}{\omega_{ac} - \omega_D} L(\tau - t)dt$$

where $\omega_D = 2(z^{tr}c_l^{tr})/a_0^2$ is the characteristic ultrasonic frequency of acoustic diffraction, and L(t) describes the temporal response of the acoustic transducer to the laser irradiation. In order to extract quantitative information about $\omega_{ac}$ in the laser-irradiated tissue, one needs to deconvolute the measured optoacoustic profile and the temporal response of the acoustic transducer, L(t).

The results of data analysis and computer calculations are then displayed showing desirable information on glucose concentration and its variation over time.

EXAMPLE 2
Opto-Acoustic Glucose Biosensor in General

Figure 2:
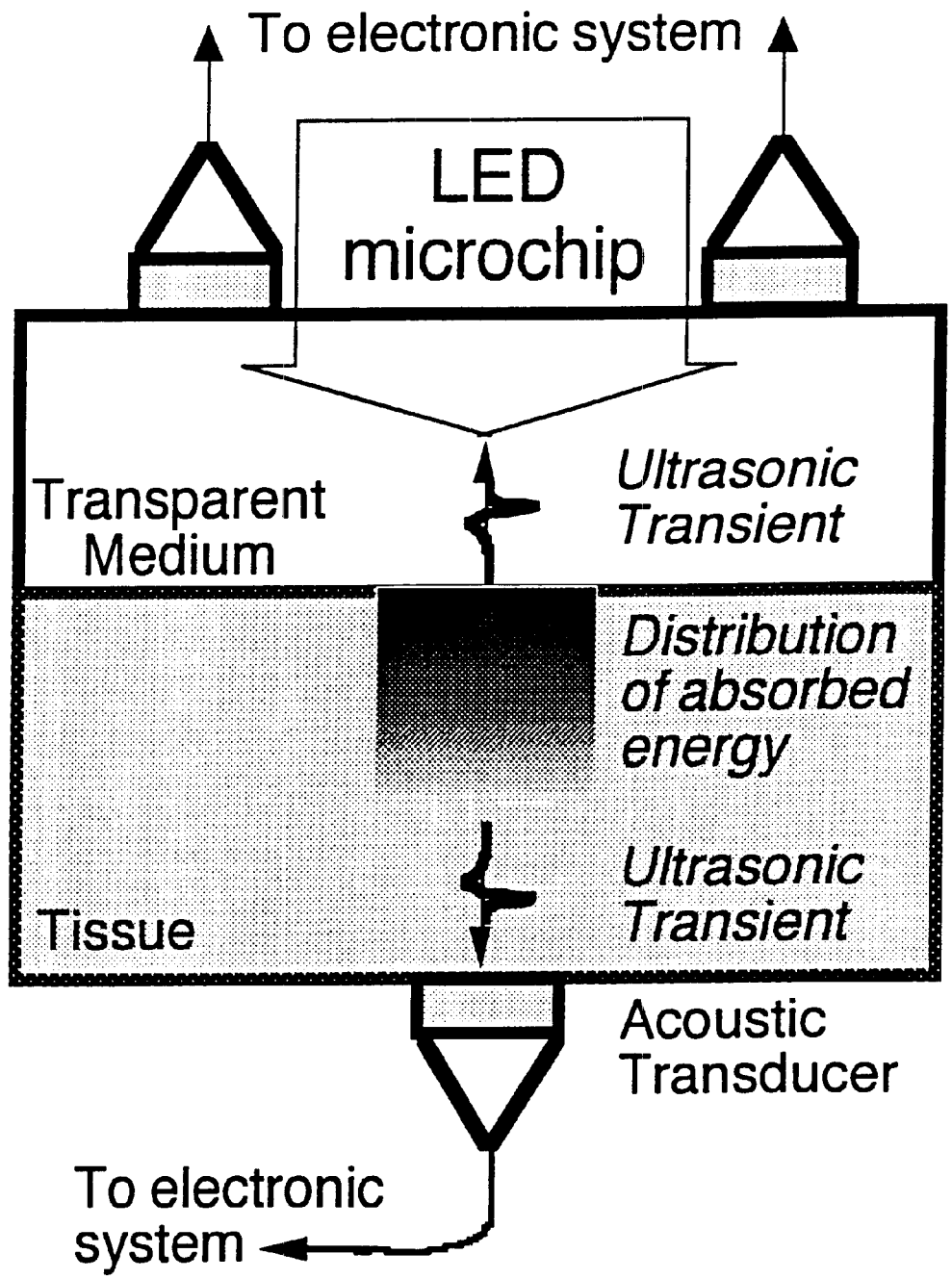
FIG. 2 shows the schematics of the opto-acoustic biosensor in general.

FIG. 2 shows more general schematic diagram of the opto-acoustic glucose biosensor. An optical fiber could be eliminated and a microlaser, manufactured as an optically emitting microchip, can be mounted directly on the opto-acoustic prism along with a wide-band acoustic detector. The acoustic detector may be placed either at the irradiated surface of tissue, or the opposite surface. Various tissues may be, in principle, used to monitor glucose. Some tissues, such as sclera, have only one surface access. In other tissues, such as ear lobe or a finger, two surfaces are readily accessible. In the latter case, it would be more convenient and technologically simpler to place acoustic transducer on tissue surface opposite to the irradiated surface. The piezoelectric transducer is designed to have minimal effective thermal noise pressure, which permits detection of 0.1% changes in tissue scattering, associated with submillimolar changes of glucose concentration. All the previously proposed noninvasive monitoring techniques fail to detect such small changes in tissue scattering.

EXAMPLE 3
Monitoring of Glucose Concentration in Sclera

Figure 3:
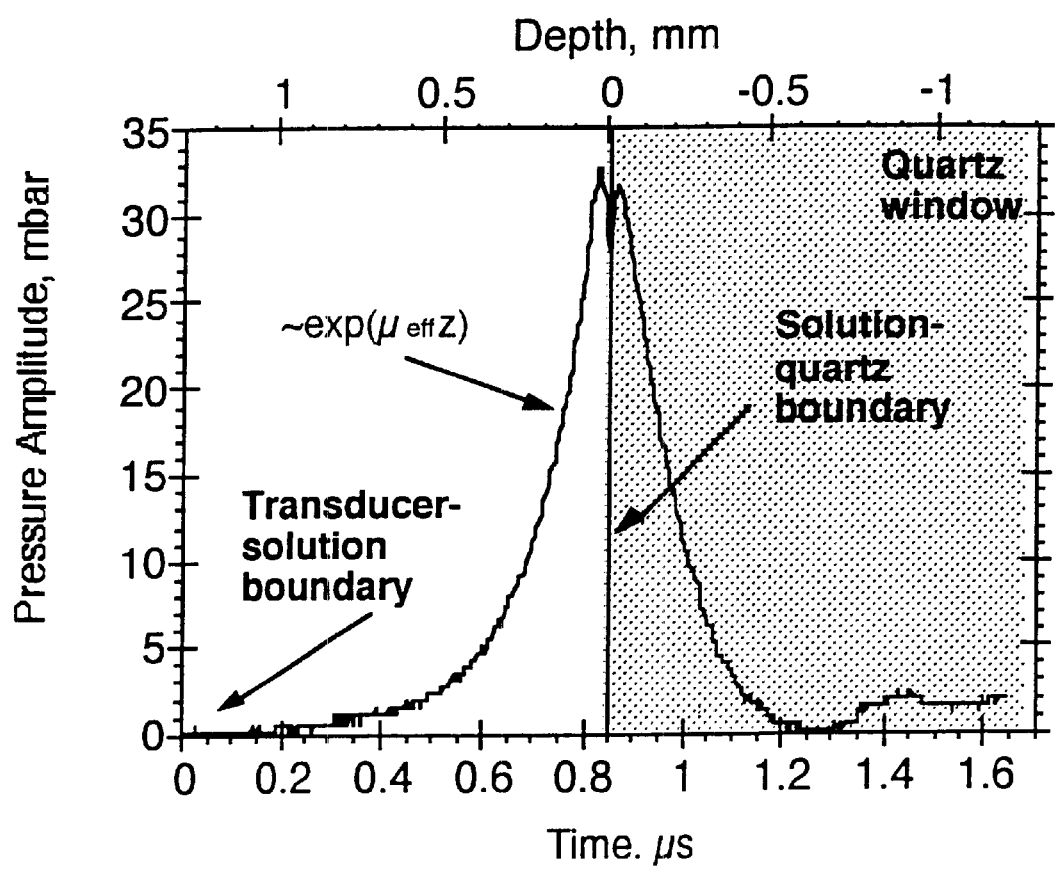
FIG. 3 shows laser-induced profile of absorbed energy distribution in optically turbid aqueous solution colored with potassium chromate, detected with a wide-band acoustic transducer at a surface opposite to the irradiated surface. This optoacoustic profile corresponds to a signal generated at rigid tissue boundary and propagated to the acoustic transducer with no acoustic diffraction.

FIG. 3 shows laser-induced profile of absorbed energy distribution in optically turbid aqueous solution colored with potassium chromate, detected with a wide-band acoustic transducer at a surface opposite to the irradiated surface. This optoacoustic profile corresponds to a signal generated at rigid tissue boundary and propagated to the acoustic transducer with no acoustic diffraction.

Figure 4:
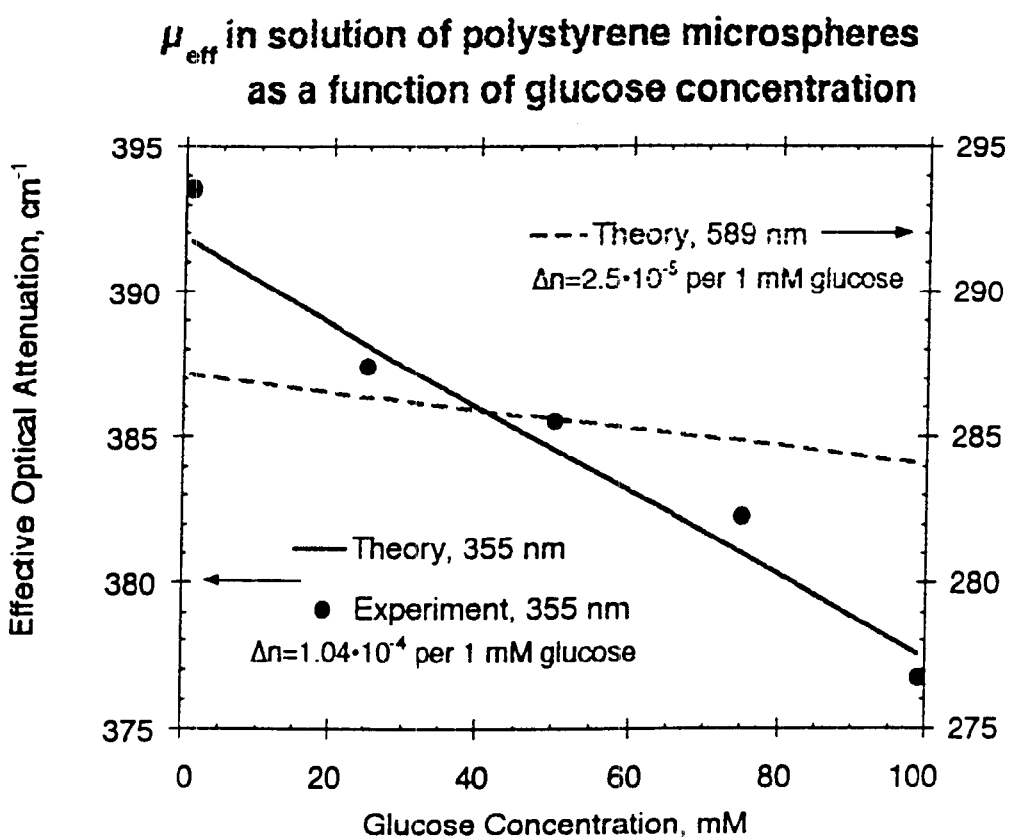
FIG. 4 shows theoretical and experimental curves of effective attenuation coefficient as a function of glucose concentration obtained from aqueous solution of polystyrene microspheres colored with potassium chromate. The measured osmotic effect of glucose on refractive index of the aqueous solution was determined as $\Delta n = 1.04 \cdot 10^{-4}$ per 1 mmole at the wavelength of 355-nm.

FIG. 4 shows theoretical and experimental curves of effective attenuation coefficient as a function of glucose concentration obtained from aqueous solution of polystyrene microspheres colored with potassium chromate. The measured osmotic effect of glucose on refractive index of the aqueous solution was determined as $\Delta n = 1.04 \cdot 10^{-4}$ per 1 mmole at the wavelength of 355-nm.

Figure 5:
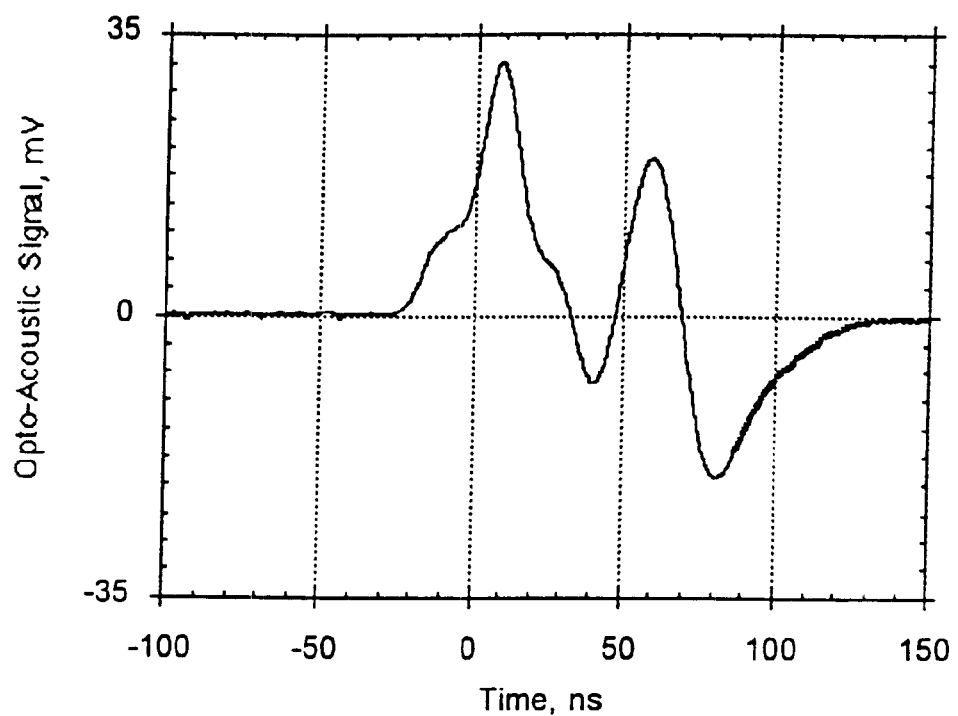
FIG. 5 shows a typical optoacoustic signal measured in vivo from rabbit sclera. The first signal (at time "0") represents a n optoacoustic profile in conjunctiva, and the second signal (at time 50-ns) represents an optoacoustic profile in sclera. Due to pronounced acoustic diffraction, the measured temporal optoacoustic profile is described by two exponents: descending $\exp(-\omega_D \tau)$ and ascending $\exp(-\omega_{ac}\tau)$, where $\omega_D$ is the characteristic ultrasonic frequency of acoustic diffraction, and $\omega_{ac}$ is the effective acoustic frequency of the optoacoustic profile in tissue. Exponential tail $\exp(-\omega_{ac}\tau)$ of the measured profile can be used for determination of the optical attenuation coefficient in sclera, which in turn is linearly related to glucose concentration.

The opto-acoustic biosensor was used for monitoring glucose concentration in sclera. A typical optoacoustic signal was measured in vivo from rabbit sclera (FIG. 5). The first signal (at time "0") represents an optoacoustic profile in conjunctiva, and the second signal (at time 50-ns) represents an optoacoustic profile in sclera. Due to pronounced acoustic diffraction, the measured temporal optoacoustic profile is described by two exponents: descending $\exp(-\omega_D \tau)$ and ascending $\exp(-\omega_{ac} \tau)$, where $\omega_D$ is the characteristic ultrasonic frequency of acoustic diffraction, and $\omega^{ac}$ is the effective acoustic frequency of the optoacoustic profile in tissue. Exponential tail $\exp(-\omega_{ac} \tau)$ of the measured profile can be used for determination of the optical attenuation coefficient in sclera, which i n turn is linearly related to glucose concentration.

Figure 6:
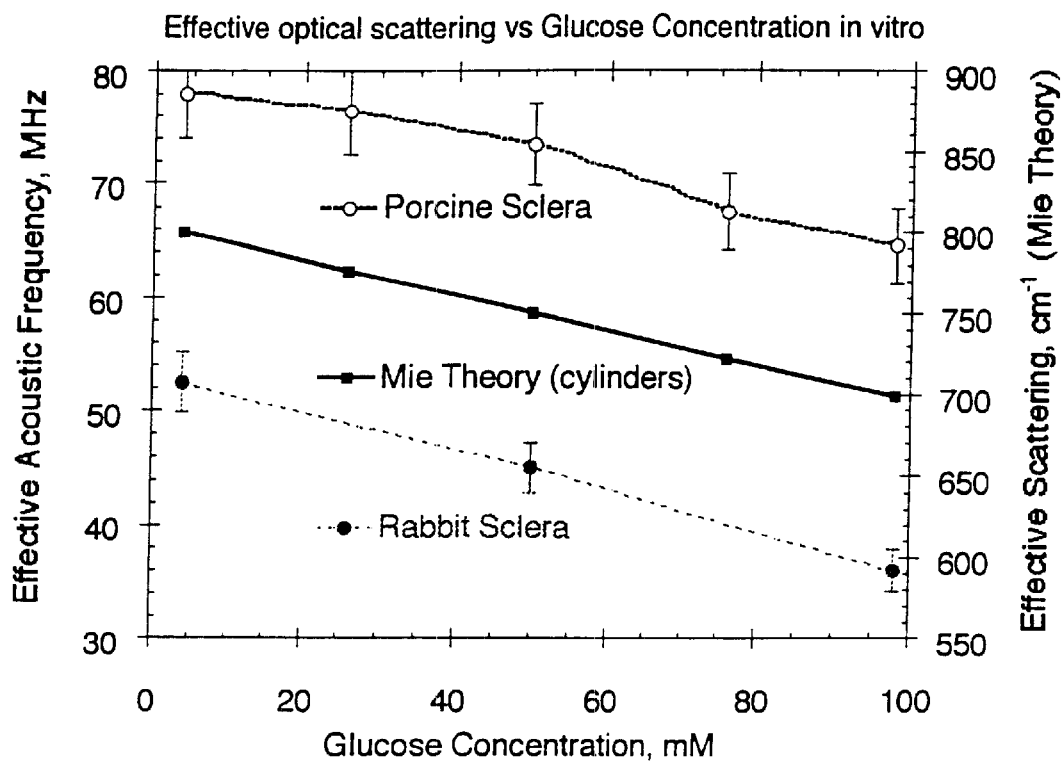
FIG. 6 shows the effective acoustic frequency of laser-induced ultrasonic transients in sclera as a function of glucose concentration. Effective optical attenuation was dominated in porcine and rabbit scleras irradiated with the wavelength of 355-nm by the optical scattering coefficient. The optical scattering in sclera was determined using invented method and system and compared with theoretical calculations using Mie theory for cylinders (collagen fibers). The theoretical curve is plotted as a function of glucose concentration on Y2 axis. The slope of theoretical curve coincides with experimentally measured slopes. Effect of glucose was found to reduce effective optical attenuation 20% with increase of glucose concentration from 1 mmole/l to 100 mmole/l.

Effective optical attenuation was dominated in porcine and rabbit scleras irradiated with the wavelength of 355-nm by the optical scattering coefficient. The optical scattering in sclera w as determined using the method; and system disclosed herein and compared with theoretical calculations using Mie theory for cylinders (collagen fibers). The theoretical curve was plotted as a function of glucose concentration on Y2 axis (FIG. 6). It shows that the slope of theoretical curve coincides with experimentally measured slopes and that the effective acoustic frequency of laser-induced ultrasonic transients in sclera is linearly related to glucose concentration. Effect of glucose was found to reduce effective optical attenuation 20% with increase of glucose concentration from 1 mmole/l to 100 mmole/l.

Figure 7:
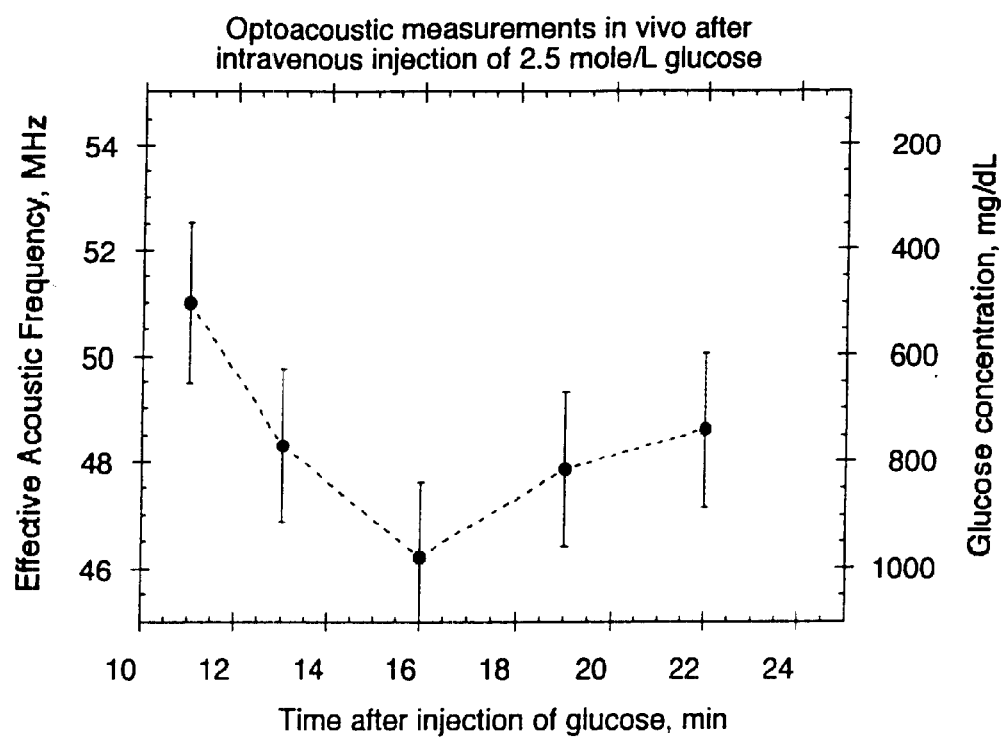
FIG. 7 shows a change in effective acoustic frequency of laser-induced ultrasonic transients measured using the disclosed technology in vivo from rabbit sclera as a function of time after intravenous injection of glucose in a rabbit. Glucose concentration in the rabbit's blood was simultaneously measured using a standard chemical blood glucose analyzer (HemoCue Inc., Calif.) and plotted on Y2 axis.

Opto-acoustic profile was measured in vivo after intravenous injection of 2.5 mol/l glucose in a rabbit. Glucose concentration in the rabbit's blood was simultaneously measured using a standard chemical blood glucose analyzer (HemoCue Inc., Calif.) and plotted on Y2 axis. A change in effective acoustic frequency of laser-induced ultrasonic transients measured in vivo from rabbit sclera is shown to be as a function of time after intravenous injection of glucose (FIG. 7).

In conclusion, the present invention discloses a method and/or system of optoacoustic biosensor for noninvasive monitoring of blood glucose. The method utilizes variation in tissue optical scattering due to the variation in concentration of glucose and its molecular derivatives. Such optoacoustic biosensor would play an important role in monitoring the level of blood glucose for diabetic patients.

The following references were cited herein.
U.S. Pat. No. 5,840,023, 1998.
U.S. Pat. No. 5,941,821, 1999.
U.S. Pat. No. 5,657,754, 1997.
PCT/GB98/00702, 1997.
U.S. Pat. No. 5,348,002, 1994.
U.S. Pat. No. 5,492,118, 1996.
U.S. Pat. No. 5,835,215, 1998.
U.S. Pat. No. 5,551,422, 1996.
U.S. Pat. No. 5,882,301, 1999.
U.S. Pat. No. 5,871,442, 1999.
U.S. Pat. No. 5,796,476, 1998.
U.S. Pat. No. 5,782,755, 1998.
U.S. Pat. No. 5,615,672, 1997.
U.S. Pat. No. 5,896,198, 1999.
U.S. Pat. No. 5,657,754, 1997.
U.S. Pat. No. 5,070,874, 1991.
U.S. Pat. No. 5,770,454, 1998.
U.S. Pat. No. 5,222,496, 1993.
U.S. Pat. No. 5,692,504, 1997.
U.S. Pat. No. 5,481,113, 1996.
U.S. Pat. No. 5,348,002, 1994.
U.S. Pat. No. 5,099,123, 1992.
*Diabetes Overview*, NIH, 94–3235 (1994).
Kohl et al., *Optics letters*, 19(24), 2170–2172 (1994).
Maier et al., *Optics Letters*, 19(24), 2062–2064 (1994).
Cote G. L., *J. of Clinical Engineering*, 22(4), 253–259 (1997).
Tuchin et al., *Proc. SPIE*, 2925: 118–142 (1996).
Larin et al., *Proc. SPIE* 3726: 576–583 (1998)
Oraevsky et al., *Proc. SPIE* 1882: 86–101 (1993).
Oraevsky et al., *Applied Optics*, 36(1), 402–415 (1997).
Oraevsky et al., *Proc. SPIE* 2681: 277–284 (1996).
Kohl et al., *Phys. Med. Biol.*, 40, 1267–1287 (1995).
Oraevsky et al., *SPIE Proc.* 2134: 122–128 (1994).
Oraevsky et al., *SPIE Proc.* 2389: 198–208 (1995).
Karabutov et al., *Appl. Phys. B*, 63: 545–563 (1996).
Oraevsky et al., *Applied Optics*, 36 (1): 402–415 (1997).
Oraevsky et al., *SPIE Proc.* 2979: 59–70 (1997).

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of noninvasive monitoring of glucose concentration in real time using laser optoacoustic imaging, comprising the steps of:

irradiating a tissue of interest with at least one optical pulse to create a distribution of absorbed optical energy in said tissue;

generating an optothermally-induced pressure profile under conditions of temporal pressure confinement in the irradiated tissue;

detecting said pressure profile with at least one wide-band acoustic transducer, wherein said acoustic transducer is capable of detecting the entire range of ultrasonic frequencies contained in said pressure profile;

recording an amplitude and temporal profile of said pressure profile by an electronic system;

analyzing the ultrasonic frequency of said pressure profile, wherein a change in the ultrasonic frequency indicates a change in tissue scattering coefficient, which in turn is proportional to a change in glucose concentration in said tissue, which correlates with a change of glucose concentration in blood.

2. The method of claim 1, wherein said tissue is selected from the group consisting of sclera, ear lobe and finger.

3. The method of claim 1, wherein said optical pulse is generated from a laser or other pulsed optical source.

4. The method of claim 1, wherein said optical pulse is in the spectral range from about 0.2 $\mu$m to about 20 $\mu$m.

5. The method of claim 1, wherein said optical pulse is in the range of nanoseconds.

6. The method of claim 1, wherein said acoustic transducer is a wide-band acoustic transducer.

7. The method of claim 1, wherein said pressure profile detection is in forward signal propagation mode as said irradiation and said acoustic detection are performed at different sites in said tissue.

8. The method of claim 1, wherein said pressure profile detection is in backward signal propagation mode as said irradiation and said acoustic detection are performed at a same site in said tissue.

9. The method of claim 1, wherein said irradiating is in a spectral range of from about 300 nm to about 2400 nm.

10. The method of claim 1, further comprising the step of: administering an exogenous substance to said tissue, wherein said substance reacts selectively with glucose and enhances the effect of glucose on tissue scattering.

11. The method of claim 10, wherein said exogenous substance is a molecules that change optical refractive index of tissue.

12. The method of claim 1, wherein said detecting step is performed by scanning of a single transducer along said tissue.

13. The method of claim 1, wherein said detecting step is performed by scanning of an array of transducers along said tissue.

14. The method of claim 1, wherein said pressure profile is recorded simultaneously from a number of sites along a surface of said tissue in order to reconstruct a two-dimensional or three-dimensional topographic image of glucose distribution in tissue.

15. The method of claim 1, wherein said irradiating is carried out with at least one optical pulse from each of two or more optical sources and/or wherein said irradiating is carried out with at least two optical pulses having at least two different wavelengths.

16. A system comprising:

a pulsed optical source to produce a pressure profile confined in a volume of tissue of interest;

a light delivery system for delivery of radiation to said tissue;

at least one wide-band acoustic transducer operating in the frequency range of from 900 kHz to 200 MHz to detect the pressure profile in said tissue, wherein said acoustic transducer is capable of detecting the entire range of ultrasonic frequencies contained in the pressure profile; and an electronic system for recording and processing of said detected pressure profile.

17. The system of claim 16, wherein said pulsed optical source generates optical pulses as short as measured in nanoseconds.

18. The system of claim 16, wherein said system is used to determine the distribution of glucose in the monitored tissue.

19. A system of claim 16, wherein said optoacoustic profile is used to monitor changing optical properties in human tissue, in order to determine optimal parameters for therapeutic or surgical treatment.

* * * * *